United States Patent [19]  
Mangold et al.

[11] Patent Number: 5,188,939
[45] Date of Patent: Feb. 23, 1993

[54] DISPLACEMENT IMMUNOASSAY UTILIZING AN OLIGAVALENT LABELLED ANTIBODY

[75] Inventors: Dieter Mangold, Maxdorf; Reiner Schlipfenbacher, Lampertheim, both of Fed. Rep. of Germany

[73] Assignee: Boehringer Mannheim GmbH, Mannheim, Fed. Rep. of Germany

[21] Appl. No.: 549,893

[22] Filed: Jul. 9, 1990

[30] Foreign Application Priority Data

Jul. 12, 1989 [DE] Fed. Rep. of Germany ....... 3922960

[51] Int. Cl.$^5$ ............................................. G01N 33/543
[52] U.S. Cl. .................................. 435/7.92; 435/7.93; 436/512; 436/518; 436/547; 436/819
[58] Field of Search ....................... 422/57, 58; 435/7.9, 435/7.93, 970, 7.92; 436/514, 538, 541, 805, 810, 169, 512, 513, 547, 819, 548, 518

[56] References Cited

U.S. PATENT DOCUMENTS

| 4,198,389 | 4/1980 | Wadsworth | 422/56 |
| 4,434,236 | 2/1984 | Freytag | 436/531 |
| 4,469,787 | 9/1984 | Woods et al. | 435/7 |
| 4,829,011 | 5/1989 | Gibbons | 436/512 |
| 4,885,255 | 12/1989 | Stock et al. | 436/512 |

FOREIGN PATENT DOCUMENTS 0173375 3/1986 European Pat. Off. .
WO82/01072 4/1982 PCT Int'l Appl. .

OTHER PUBLICATIONS

Ishikawa et al., Eds. Enzyme Immunoassays, Igaku-shoin, Tokyo JP, pp. 81-88, (1981).

Primary Examiner—David Saunders
Assistant Examiner—Christopher L. Chin
Attorney, Agent, or Firm—Felfe & Lynch

[57] ABSTRACT

A method for carrying out competitive displacement immunoassays which entails the use of an oligovalent labelled antibody having at least 4 binding sites for the analyte to be determined per label.

9 Claims, 2 Drawing Sheets

DISPLACEMENT IMMUNOASSAY UTILIZING AN OLIGAVALENT LABELLED ANTIBODY

FIELD OF THE INVENTION

The subject matter of the invention is a method for the determination of an analyte as well as a reagent which can be used for this method.

BACKGROUND AND PRIOR ART

The determination of analytes is a widespread concern, especially in clinical diagnostics. Recently methods which comprise immunological reaction steps have, above all, been applied for this because of the great accuracy which can be achieved, as well as their wide applicability. Because of the advantage of easy handling, such methods are increasingly being carried out with the aid of a component of an immunological reaction bound to a solid phase. These methods allow, e.g., the use of test strips on which the entire reaction sequence proceeds solely by bringing the sample into contact with the strip.

Immunological methods of determination can be classified according to the nature of the participating reaction partners. One of these is the so-called competitive displacement test. In this procedure a bound, immobilized antigen, to which a labelled antibody is itself bound, is brought into contact with the sample. In the presence of analyte in the sample the immobilized analyte is displaced from the immunocomplex of immobilized antigen and labelled antibody by the analyte in the sample. The previously immobilized labelled antibody thus passes to the liquid phase, forms a complex with the analyte to be determined, and can be determined by means of its label after separating the liquid phase from the solid phase. The concentration of the analyte in the sample can be determined from this.

Such an immunotest is described for example in EP-A-0173375. A labelled Fab fragment is used as the labelled antibody which is present at the beginning of the test in a complex with the immobilized analyte.

A similar method is described in U.S. Pat. No. 4,436,236; however, an immobilized antigen is used which has a lower affinity to the labelled antibody than the analyte. Labelled antibody fragments are also preferably used in this method.

The methods of EP-A-0173375 and U.S. Pat. No. 4,436,236 are disadvantageous in that they exhibit high blank values for the measurement even if no analyte is in the sample; the magnitude of the signal is, however, relatively small.

An immunoassay is described in U.S. Pat. No. 4,277,560 in which a labelled analyte is bound reversibly to a solid phase via an immobilized antibody. The labelled analyte is displaced from the solid phase by the analyte present in the sample and can be used subsequently as a measure for the amount of analyte to be determined. This method is disadvantageous in that the accuracy of the results depends very strongly on the uniformity of the coating of the solid phase. Adequate accuracy is only achievable with difficulty.

SUMMARY OF THE INVENTION

The object of the present invention is therefore to provide a method for the determination of an analyte in which the disadvantages of the methods according to the state of the art are avoided, in particular the relatively high blank values and the complicated measures necessary for their production. The method should be accurate and easily automated.

The object of the invention is achieved via a method for determining an analyte in a liquid sample, comprising contacting the liquid sample to an immobilized immunocomplex of an analyte or analyte analogue and labelled, oligomeric antibody, wherein said labelled oligomeric antibody reacts with both the analyte in the liquid sample and the analyte or analyte analogue of the immobilized immunocomplex, and is immobilized by binding to the immobilized analyte or analyte analogue. The oligomeric antibody is characterized by at least 4 binding sites for the analyte or analyte analogue per label.

"Oligovalent antibody" as used herein refers to an antibody which has at least 4, and preferably from 6 to 12 binding sites for analyte or analyte analogue per label.

A reagent for carrying out the above-mentioned method is also an object of the invention.

The analyte which can be determined in the method according to the present invention is, in particular, an antigen or a hapten. The determination can be carried out qualitatively, i.e., in order to establish whether the analyte is present in the sample. However, it can also be used for the quantitative determination of the concentration of the amount of an analyte in the sample. The liquid sample is preferably an aqueous solution, suspension or emulsion. Particularly preferred are body fluids or fluids derived therefrom such as blood, serum, plasma or urine.

The concentration of the analyte can be determined with the proposed method in a range of $10^{-9}$ up to $10^{-5}$ mol/l preferably of $10^{-8}$ up to $10^{-6}$ mol/l. Particularly preferred is the determination of so-called highly concentrated analytes; such analytes are those present in a concentration range greater than $10^{-8}$ mol/l. Examples of such analytes in urine are albumin or $\alpha_1$-microglobulin ($\alpha_1$M).

An analyte analogue is to be understood as a substance which is immunologically similar to the analyte. Although the analogue does differ structurally from the analyte, it is, however, recognized by an antibody to the analyte. Within the scope of the present invention those analyte analogues can be used, for example, which are bound more strongly by the labelled antibody than the analyte itself. In this case the blank value i.e. the measurement result in the absence of the analyte is especially low. Examples of such analyte/analyte analogue pairs are porcine albumin/human albumin, and simian albumin/human albumin.

Immobilized analytes or analyte analogues are analytes or analyte analogues bound to a solid phase. The binding can be covalent, precipitative, via specific interactions or adsorptive. Each of these types of binding can be used provided the analyte or analyte analogue does not become detached to a great extent from the solid phase. Well-known methods are known to the expert for each of these types of binding. The type of solid phase depends on the type of binding of the analyte or analyte analogue. For example, if the analyte is bound covalently, a solid phase should be used which has reactive groups. When the binding is by means of specific interactions, the binding is preferably via biotin/streptavidin. The solid phase is then, for example, provided with a coating containing streptavidin and the analyte or analyte analogue bound to it is bound covalently to biotin. Quite a strong binding is formed via streptavidin and biotin. The solid phase can be present in the form of particles, papers, materials for pads, membranes, tissues or also cuvettes, microtiter plates etc. If the method of detection is to be carried out on a test strip, adsorptive pads are preferred.

A labelled antibody in the method according to the present invention is an antibody which can enter into an immunological reaction with the analyte to be determined as well as with the immobilized analyte or analyte analogue. Antibodies against the analyte or analyte analogue can be produced and selected by known methods. Polyclonal as well as monoclonal antibodies can be used, monoclonal antibodies being preferred.

The label can be any substance by which the presence of the antibody can be detected either quantitatively or qualitatively. Suitable labels include for example, enzymes, metals, residues whose emission or absorbance of light or radioactive radiation can be measured, or residues which can be converted into such residues by a chemical or immunological reaction. A wide selection of labels is available to those skilled in the art. One requirement of the label is that it must be possible to attach several antibody binding sites to this label. Therefore the label preferably has reactive groups, for example, hydroxy, amino, mercapto or carboxyl groups which can be linked directly or indirectly to the antibodies.

Enzymes which are suitable as the label are, for example hydrolase such as $\beta$-galactosidase or peroxidases such as POD.

Metals, especially those in the form of finely dispersed particles, for example colloids, include for example, gold. Such labels are described, e.g., in EP-A-0258963. Fluorescent compounds include resorufins; colored compounds include phycoerythrin, dyed latex particles and dyed tellurium and selenium oxides (EP-A-0298368). Preferred labelling agents are enzymes and metals. Enzymes are especially preferred. The labelled oligovalent antibody of the method according to the present invention has, in contrast to the antibodies known to the art, at least 4, preferably 6 to 12 binding sites for the analyte or the analyte analogue. In the following such a labelled antibody is denoted an "oligovalent, labelled antibody".

In order to label the oligovalent antibody it is preferred to react a label with several antibodies which have fewer binding sites, for example 1 or 2 binding sites, such as Fab fragments or IgG.

In the process for the production of labelled oligovalent antibodies, mixtures of labelled antibodies are often produced which have different numbers of binding sites. Mixtures of labelled antibodies, i.e., labelled antibodies with a definite number of binding sites, for example with 4 to 7 binding sites per label, can be isolated from this mixture. These mixtures can be used advantageously in the method according to the present invention when they contain, for the most part labelled antibodies with at least 4 binding sites per label.

The binding of 5 IgG or 10 Fab fragments onto the enzyme is particularly advantageous for enzyme-labelled antibodies.

The production of such labelled oligovalent antibodies is known and described for example in Kitigawa in Enzyme Immunoassay (Eds. Ishikawa, Kuwai, Migui; Igaku Shoin Tokyo/New York (1981), p. 81–89).

It is preferred to use a mixture of immobilized analytes or analyte analogues and labelled antibodies as an immobilized immunocomplex of these components. Such a solid phase containing an immunocomplex which contains the labelled antibody which can be displaced by the sample analyte is also called a displacement matrix in the text which follows.

To produce this, an immobilized immunocomplex is formed from the already immobilized analyte or analyte analogue and the labelled antibody in an immunological reaction.

A further method for the production of such a displacement matrix is to carry out an immunological precipitation reaction between the analyte or analyte analogue and an antibody to the analyte or to the analogue on the solid phase. Subsequently it is reacted with the labelled antibody. Such a method is, for example, described in EP-A-O 312 907.

If the analyte or analyte analogue is to be immobilized by means of specific interactions, such as biotin/streptavidin, a biotinylated analyte or biotinylated analyte analogue is converted into a soluble immunocomplex in an immunological reaction with the labelled antibody and this is then brought into contact with a solid phase coated with streptavidin. A displacement matrix is obtained after separation of the liquid phase, even without washing steps, which is virtually uncontaminated by non-complexed labelled antibodies or excess label. It is also possible to bring the biotinylated analyte or analyte analogue into contact with the solid phase coated with streptavidin in a first reaction.

The following ratios of the components have proven to be especially advantageous: as the concentration of the analyte to be determined increases, the amount of immobilized analyte/analyte analogue should also increase. If the chosen amount of labelled antibody is too low in relation to the amount of analyte or analyte analogue, then in some cases the method performs poorly.

The amount of immobilized analyte or analyte analogue is preferably 1 ng–0.1 mg/cm$^2$ matrix, an especially preferred particularly range is 0.1 $\mu$g–10 $\mu$g/cm$^2$ matrix. The amount of labelled antibody is 1–1000 mU/cm$^2$, preferably 10–500 mU/cm$^2$ matrix.

The method according to the present invention is in general carried out analogously to the well-known principles for competitive displacement tests, in which, however, the displacement method according to the present invention is used.

The method is particularly suitable for the analysis of small amounts of sample. Sample volumes of 5 $\mu$l to 1 ml are suitable for the investigation by means of conventional test strips. The volumes are dependent on the absorptivity of the matrices used. The sample volumes preferably do not exceed the absorptive volumes of the matrices.

At the start of the method according to the present invention, the sample volume is brought into contact with the immobilized analyte or analyte analogue and left there for a defined time. During this time, in the presence of the analyte to be determined in the sample, the immobilized analyte or immobilized analyte analogue is displaced competitively from the immunocomplex of labelled oligovalent antibody and immobilized analyte or analyte analogue, and is replaced by the analyte from the sample. A soluble or free immunocomplex is formed or sample analyte and labelled antibody. The more analyte present in the sample, the more soluble immunocomplex is formed. Therefore, it is possible to determine the amount of analyte from the amount of labelled antibody remaining on the solid phase or from the labelled antibody present in the liquid phase. For this, the liquid phase is at least partially separated from the solid phase. Then the amount of label in one of the two phases is determined in the usual way. If the label is an enzyme, then the phase is reacted with a substrate under conditions which are suitable for the enzyme reaction. The amount of reacted substrate is likewise a measure for the amount of analyte in the sample.

By carrying out the method according to the present invention with samples containing known concentrations of analyte, a calibration curve is obtained from which the concentration of analyte is a sample of hitherto unknown analyte content can be read off from the measurements thus obtained.

The method can be carried out via different embodiments:

In one embodiment, sample containing analyte is pipetted into an Eppendorf tube with a test zone containing the immobilized analyte or analyte analogue and the enzyme-labelled antibody. After shaking, for example, for 5 minutes, part of the solution is transferred into a cuvette which contains a chromogenic substrate for the enzyme.

The rate of color formation is measured by measurement of the absorbance at a wavelength at which the colored product formed absorbs light.

In a further embodiment, the sample is added to a cuvette which has a test zone as described above and the mixture is incubated for a time and the liquid phase is removed from the cuvette. A washing step can follow afterwards in order to completely remove any remaining liquid phase. Subsequently, a solution of a chromogenic substrate for the enzyme label is added to the cuvette. Also, in this case, the change in color is measured. In contrast to the embodiment described above, the change in color decreases as the amount of analyte present in the sample increases.

DETAILED DESCRIPTION OF PREFERRED EMBODIMENTS

Figure 1:
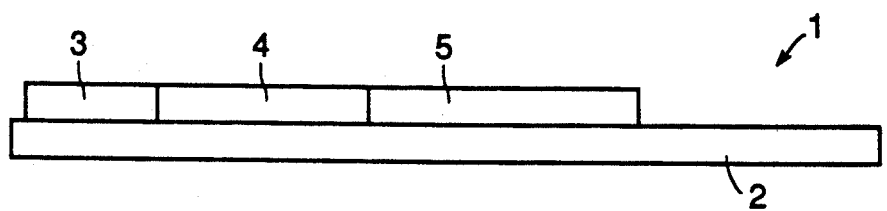
FIG. 1 shows a longitudinal section through a chromatography strip.

A particularly preferred embodiment is a chromatographic strip according to FIG. 1. The strip is composed of a supporting foil on which an absorptive pad 3, a displacement matrix 4 and a substrate pad 5 are mounted and adsorptively joined to one another. The strip 1 is placed in the sample liquid such that, of the pads, only the absorptive pad 3 comes into contact with the sample. The use of absorptive pads is particularly preferred but is not absolutely essential. The sample is drawn from there into the displacement matrix 4. This displacement matrix is, for example, an absorptive pad on which the analyte or the analyte analogue is immobilized and which contains the labelled oligovalent antibody in the form of an immunocomplex with the immobilized analyte or analyte analogue. In this case, the analyte to be determined displaces the immobilized analyte or analyte analogue from the immunocomplex with the oligovalent labelled antibody. The soluble complex thus formed flows with the sample fluid into zone 5 on which the chromogenic substrate suitable for the enzyme label is present in an impregnated form. The change in color is measured in the substrate zone 5. If desired, a fabric which absorbs slowly can be mounted between the displacement matrix 4 and substrate zone to delay the flow of liquid.

Figure 2:
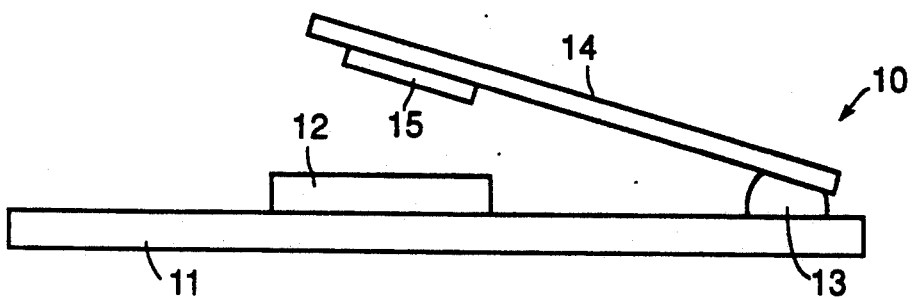
FIG. 2 shows a longitudinal section through a test strip with flap.
Figure 3:
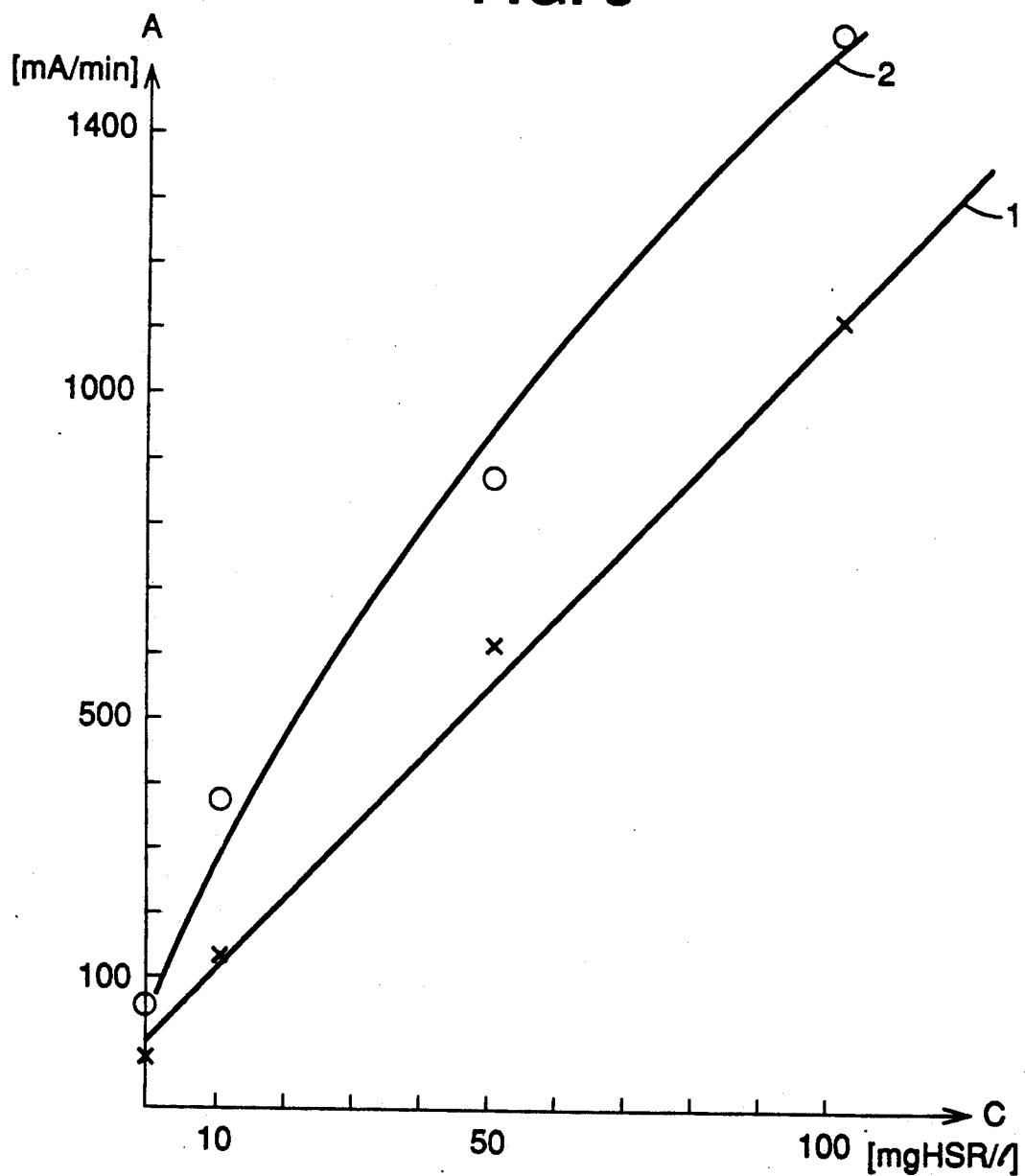
FIG. 3 shows a calibration curve for the determination of albumin.

A further embodiment is a test strip 10 according to FIG. 2.

A displacement matrix 12 containing the immobilized analyte or analyte analogue as well as the labelled antibody is fixed onto a supporting foil 11. An at least partially transparent, movable flap 14 is mounted on the supporting foil, for example, by means of an adhesive patch 13. A film 15 containing the chromogenic substrate is located on the side facing the displacement matrix. After the incubation period the film 15 is pressed onto the matrix 12 by lowering the flap and by this means the reaction for the determination is started. A test with this test strip can be evaluated, e.g., photometrically as well as reflectrophotometrically by the additional use of reflecting components.

The method according to the present invention has the advantage that the blank value is relatively small compared to the measurement signal. In addition, it has turned out that contamination of the labelled antibody used with non-binding impurities such as excess labelling agent has to be taken into account when using competitive displacement tests of the prior art. These impurities have to be removed, for example by washing the displacement matrix containing the immunocomplex of immobilized analyte or analyte analogue and labelled antibody of the prior art before carrying out the test. Contamination by reacted labelling agent is largely avoided as a result of the favorable ratio of binding sites to the labelling agent in the labelled oligovalent antibody of the method according to the present invention. A further advantage of the method according to the present invention is that it requires particularly few steps and matrices: as a conseuqence complicated, expensive and time-consuming steps are obviated.

A further object of the invention is a reagent to carry out the method according to the present invention in order to determine an analyte in a sample which contains an immobilized antibody which can enter into an immunological reaction with the analyte to be determined as well as with the immobilized analyte or immobilized analyte analogue in which the labelled antibody has at least four binding sites per label for the analyte or the analyte analogue.

The following Examples elucidate the invention further:

EXAMPLE 1

Determination of albumin

1. Production of the displacement matrix a) Cross-linking of human serum albumin (HSA) to polyhuman serum albumin (pHSA) by means of disuccinidylsuberate (DSS)

2.5 ml of a solution of 50 mg DSS/ml dioxan was added within 2 hours to 1.5 HSA which was present in 30 ml potassium phosphate buffer, 200 mM, pH 8.0. Afer the cross-linking reaction was completed, it was dialyzed against a 500-fold volume of potassium phosphate buffer, 20 mM, pH 7.2. The high molecular fraction (pHSA) with a molecular weight of more than 650000 Dalton was separated off by gel filtration on Superose 6 ® (Pharmacia, Frieburg, German Federal Republic) and lyophilized after addition of 6 mg saccharose/mg protein.

b) Immobilization of human serum albumin

Pads of 6×8 mm size and 0.5 mm thickness and made of 50% polyester/50% linters were impregnated with 15 μl of a solution of 30 mg/l in 10 mM sodium phosphate buffer pH 7.5 and dried for 30 minutes at 50° C.

c) Conjugates of antibodies to HSA and β-galactosidase

The conjugates I to XI were produced from IgG (clone 1 (I-III) or 2 (IV-VII), or Fab (clone 3 (VII-XI) according to the instructions of T. Kitiwaga (Enzyme Immunoassay, publisher: Ishikawa, Kawai, Migui; Igaku Shoin Tokyo/New York 1981, p. 81 -89) or E. Ishikawa (1983), J. Immunoassay, 4 (3), 209–327, and each was fractionated by Superose 6® chromatography:

Introduction of maleimide groups into IgG
Add to a solution of 1.4 mg (9.3 nmol) IgG in 0.5 ml sodium phosphate buffer, 0.1 mol/l; pH 7.0, 50/ul of 0.9 g/l 3-maleimidobenzoyl-N-hydroxy-succinimide ester (MBS) in N,N-dimethylformamide.
Incubate the reaction mixture at 30° C. for 30 min and then pass it over a Sephadex G-25 (1.0×45 cm) column using sodium phosphate buffer, 0.1 mol/l; pH 6.5 as elution fluid.

Conjugation
For conjugation dissolve 1.5 mg (2.8 nmol) β-Galactosidase lyophilized in 1.4 ml sodium phosphate buffer, 0.1 mol/l; pH 6.5 containing 1.25 mg (8.3 nmol) of maleimide-IgG. The final concentrations of IgG and the enzyme are 6 and 2/umol/l, respectively.
Now incubate the reaction mixture at +4° C. for 20 h.
Pass it over a Sepharose 6 B column (1.5×45 cm) using as elution fluid sodium phosphate buffer, pH 6.5, 10 mmol/l containing 0.1 mol/l NaCl, 1 mmol/l MgCl$_2$, 1 g/l NaN$_3$.
Read absorption at 280 nm of elution fluid.
Pool fractions according to elution profile.
Determine β-Galactosidase activity in the pools.

| | | |
|---|---|---|
| I | ca. 4–7 | IgG per molecule β-galactosidase |
| II | 2–5 | IgG per molecule β-galactosidase |
| III | 1–2 | IgG per molecule β-galactosidase |
| IV | 4–7 | IgG per molecule β-galactosidase |
| V | 3–5 | IgG per molecule β-galactosidase |
| VI | 2–3 | IgG per molecule β-galactosidase |
| VII | 1–2 | IgG per molecule β-galactosidase |
| VIII | 8–14 | Fab fragments per molecule β-galactosidase |
| IX | 6–10 | Fab fragments per molecule β-galactosidase |
| X | 4–8 | Fab fragments per molecule β-galactosidase |
| XI | 1–4 | Fab fragments per molecule β-galactosidase | d) Displacement matrix

15 μl of a solution of the conjugate (4 U/ml) from c) in 0.1 M HEPES buffer (pH 7.5) containing 0.5% bovine serum albumin was added dropwise onto a pad from b). Afterwards, the pad was dried.

e) Determination of the blank value and the measurement range

A stack of two 6×8 mm pads from d) was impregnated with 55 μl buffer solution (50 mmol/l phosphate pH 7.5) containing
A) 0 mg/l human serum albumin (HSA)
B) 100 mg/l After 5 minutes the liquid was centrifuged from the matrix. 5 mmol/l chlorophenol-red-β-galactoside was added to the liquid and the increase in absorbance at 576 nm was measured in a cuvette at 37° C. by means of a photometer.

The blank value was derived from the measurement A) i.e., the value which simulates a signal even in the absence of the analyte.

The measurement from B) correspond to the signal amplitude for 100 mg/l analyte.

The quotient of signal amplitude to blank value is a measure for the attainable accuracy of the test.

Table 1 shows the blank value (A), the measured value (B) and the quotients B/A for the individual conjugate mixtures I to XI:

| conjugate | blank value (A) [mA/min] | measurement value (B) [mA/min] | B/A |
|---|---|---|---|
| I | 55 | 1190 | 21.6 |
| II | 175 | 1900 | 10.8 |
| III | 520 | 2370 | 4.5 |
| IV | 70 | 940 | 13.4 |
| V | 70 | 1385 | 19.7 |
| VI | 385 | 2175 | 5.6 |
| VII | 1330 | 2300 | 1.7 |
| VIII | 80 | 580 | 7.2 |
| IX | 106 | 660 | 6.2 |
| X | 180 | 1000 | 5.5 |
| XI | 310 | 1060 | 3.4 |

It is clearly apparent that greater accuracy can be achieved using the labelled antibodies which have the most binding sites. The higher B/A, the better the accuracy of the test.

2. Recording of calibration curves for the determination of albumin

Pads of 6'8 mm size and 0.5 mm thickness and made of 50% polyester/50% linters were impregnated with 15 μl of a solution of 50 or 100 mg/l pHSA in 0.01 mmol/l phosphate buffer pH 7.25 and dried. Afterwards, each of the pads is impregnated with 15 μl of a solution of 4 U/ml of the labelled antibody I in HEPES buffer (100 mmol, pH 7.5)+0.5% BSA and dried.

Both pads B and C, produced in this way, are suitable for the determination of albumin. In order to record their calibration curves they were impregnated with samples which contained 0 mg/l, 10 mg/l, 50 mg/l or 100 mg/l HSA. After 5 minutes the liquid was separated from the pad by centrifugation and 5 mmol/l chorophenol-red-β-galactoside (CPRG) was added to the liquid. The increase in absorbance A (mA/min) was determined photometrically as described under e).

The calibration curves for the pads B and C are shown in FIG. 2. Curve I depicts the absorbance timecourse for the pad B which was impregnated with 50 mg/l pHSA and curve II was obtained using the pad C impregnated with 100 mg/l pHSA.

3. Determination of an unknown content of albumin

In order to determine albumin, 25 μl sample of unknown albumin content is added to a pad B or C; after 5 minutes the sample liquid was removed, CPRG was added and also the increase in absorbance A is measured. The albumin content ma be inferred from the value obtained by means of the calibration curve.

EXAMPLE 2

Determination of $\alpha_1$-microglobulin

Production of the displacement matrix a) Production of a pad coated with thermo-BSA streptavidin Thermally aggregated BSA, which is denoted thermo-BSA infra. was produced in the following way: 1 g BSA was dissolved in 100 ml 50 mmol potassium phosphate solution at a pH of 7.0, heated to 70° C. and maintained at this temperature for 4 hours while stirring gently. The solution was cooled, filtered and adjusted to a concentration of 50 mg/ml. Subsequently, it was dialyzed against a 30-fold volume of redistilled water.

Production of a conjugate of streptavidin with thermo-BSA: Streptavidin isolated from *Streptomyces avidinii* was reacted with maleimido-hexanoyl-N-hydroxysuccinimide and as a result streptavidin with maleido groups was obtained. Theremo-BSA was reacted with S-acetyl-mercaptosuccinic acid anhydride and subsequently the protected SH-groups were released by addition of hydroxylamine. The streptavidin containing maleimido groups was then mixed with the thermo-BSA containing SH-groups during which the desired conjugate is formed.

Pads of 6×8 mm size and 0.5 mm thickness, made of 50% polyester/50% linters were impregnated with 15 μl of a solution of 200 mg/l thermo-BSA streptavidin in 10 mM sodium phosphate buffer pH 7.5 and dried for 30 minutes at 50° C.

b) Production of biotinylated $\alpha_1$-microglobulin analogous to the instructions "Biotinylierung Monoklonaler Antikörper" (according to Peters, Baumgarten, Schulze: Monoklonaler Antikörper, Herstellung und Charakterisierung; Verl. Springer 1985).

c) Conguates of monoclonal antibodies directed toward $\alpha_1$-M and $\beta$-galactosidase The conguate ws produced according to the instructions of T. Kitiwaga in Enzyme Immunoassay (Eds. Ishikawa, Kuwai, Migui; Igaku Shoin Tokyo/New York (1981) pp 81–89) and fractionated into the pools I and II using Superose ™ 6 chromatography (see example 1). Pool I: 3–7 IgG/ $\beta$Gal, pool II: 1–3 IgG/$\beta$Gal d) Displacement matrix 15 μl of a solution of 50 mg/l biotinylated $\alpha_1$-microglobulin in 10 mmol/l phosphate buffer pH 7.5 was added dropwise onto a pad from a). Subsequently, the pad was dried. Afterwards, 15 μl of a solution of 4 U/ml conjugate I (pad D) or conjugate II (pad E) in 0.1 mol/1 HEPES buffer (pH 7.5) containing 0.5% BSA was added dropwise onto it.

As in Example 1 the blank value A or the signal amplitude B was measured (see Table 2) in the determination of the samples:
A 0 mg $a_1$M/l
B 100 mg $a_1$M/l

| conjugate | blank value (A) [mA/min] | measurement value (B) [mA/min] | B/A |
|---|---|---|---|
| I | 175 | 803 | 4.6 |
| II | 327 | 960 | 2.9 |

Also, in this case, it is apparent that the blank value increases out of proportion with the decrease in the number of binding sites of the labelled antibody.

The recording of the calibration curve and the determination of an unknown content of αl-microglobulin in a sample is carried out analogous to Example 1.

It will be understood that the specification and examples are illustrative but not limitative of the present invention and that other embodiments within the spirit and scope of the invention will suggest themselves to those skilled in the art.

We claim:

1. Method for determining an analyte in a liquid sample, comprising contacting said liquid sample to an immobilized complex of (i) immobilized analyte or analyte analogue and (ii) an obligovalent labelled antibody which binds to said analyte to be determined, said oligovlent labelled antibody produced by conjugating antibodies having 2 or fewer binding sites and characterized by at least 4 binding sites for said analyte or analyte analogue per label, under conditions favoring displacement of said obligovalent labelled antibody from said immobilized analyte or analyte analogue and formation of soluble complexes of analyte to be determined and oligovalent labelled antibody, and determining oligovalent labelled antibody bound to said immobilized analyte or analyte analogue or in said liquid sample as a determination of analyte to be determined.

2. Method of claim 1, wherein said analyte to be determined is present in a concentration greater than $10^{-8}$ mol/l.

3. Method of claim 1, wherein said analyte to be determined is present in a concentration from $10^{-9}$ mol/l to $10^{-5}$ mol/l.

4. Method of claim 1, wherein said analyte is albumin.

5. Method of claim 1, wherein said analyte is $\alpha_1$-microglobulin.

6. Method of claim 1, wherein said oligovalent labelled antibody has from 6 to 12 binding sites for said analyte per label.

7. Method of claim 1, wherein said oligovalent labelled antibody comprises a mixture of antibodies having from 4 to 7 binding sites for analyte per label.

8. Method of claim 1, wherein said oligovalent labelled antibody comprises 5 IgG molecules and enzyme label.

9. Method of claim 1, wherein said oligovalent labelled antibody comprises 10 Fab fragments and an enzyme label.

* * * * *

UNITED STATES PATENT AND TRADEMARK OFFICE
CERTIFICATE OF CORRECTION

PATENT NO. : 5,188,939
DATED : February 23, 1993
INVENTOR(S) : Dieter Mangold et al It is certified that error appears in the above-indentified patent and that said Letters Patent is hereby corrected as shown below:

Column 4, line 64, change "formed or sample" to --formed or sample--.
Column 7, line 12, change " (IV-VII), or Fab (clone 3 (VII-XI)" to
--(IV-VII)), or Fab (clone 3 (VIII-XI))--.
Column 7, line 65, change "15 ul" to --15 µl--.
Column 8, line 48, change "6'8" to --6x8--.

Signed and Sealed this

Second Day of August, 1994

Attest:

BRUCE LEHMAN

Attesting Officer    Commissioner of Patents and Trademarks